United States Patent
Lane

(10) Patent No.: US 10,506,165 B2
(45) Date of Patent: Dec. 10, 2019

(54) CONCUSSION SCREENING SYSTEM

(71) Applicant: Welch Allyn, Inc., Skaneateles Falls, NY (US)

(72) Inventor: John A. Lane, Weedsport, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 165 days.

(21) Appl. No.: 14/927,171

(22) Filed: Oct. 29, 2015

(65) Prior Publication Data

US 2017/0124699 A1   May 4, 2017

(51) Int. Cl.
| | |
|---|---|
| G06T 7/00 | (2017.01) |
| G06T 7/20 | (2017.01) |
| G06K 9/00 | (2006.01) |
| H04N 5/232 | (2006.01) |
| H04N 7/18 | (2006.01) |
| H04N 5/225 | (2006.01) |

(52) U.S. Cl.
CPC ..... *H04N 5/23293* (2013.01); *G06K 9/00604* (2013.01)

(58) Field of Classification Search
None
See application file for complete search history.

(56) References Cited

U.S. PATENT DOCUMENTS

| | | |
|---|---|---|
| 3,602,580 A | 8/1971 | Samuels |
| 3,879,113 A | 4/1975 | Howland et al. |
| 4,523,820 A | 6/1985 | Kaakinen |
| 4,586,796 A | 5/1986 | Molteno |
| 4,669,836 A | 6/1987 | Richardson et al. |
| 4,758,080 A | 7/1988 | Howland |
| 4,834,528 A | 5/1989 | Howland et al. |
| 4,950,069 A | 8/1990 | Hutchinson |
| 4,989,968 A | 2/1991 | Freedman |
| 5,214,456 A | 5/1993 | Gersten |

(Continued)

FOREIGN PATENT DOCUMENTS

| | | |
|---|---|---|
| EP | 0 962 184 A1 | 12/1999 |
| EP | 1 308 128 A2 | 5/2003 |

(Continued)

OTHER PUBLICATIONS

"A Portable, Scalable Retinal Imaging System," TI Engibous Competition Report (Spring 2012), Rice University, http://www.ti.com/corp/docs/university/docs/Rice_University_mbileVision%20Final%20Report.pdf (96 pages).

(Continued)

*Primary Examiner* — Frederick D Bailey
(74) *Attorney, Agent, or Firm* — Merchant & Gould P.C.

(57) ABSTRACT

A concussion screening device includes an illumination unit, an image sensor array, a processing unit, and system memory. The concussion screening device displays stimuli on the illumination unit and receives a plurality of images on the image sensor array. The stimuli correspond to a concussion test. The processor processes the plurality of images, which includes detecting one or more pupils of an evaluated person during the concussion test. Based on the processing, the concussion screening device determines whether or not an evaluated person has suffered a concussion. The results are displayed to a user and/or the evaluated person.

20 Claims, 7 Drawing Sheets

(56) References Cited

U.S. PATENT DOCUMENTS

| | | |
|---|---|---|
| 5,329,322 A | 7/1994 | Yancey |
| 5,355,895 A | 10/1994 | Hay |
| 5,502,520 A | 3/1996 | Cibis et al. |
| 5,632,282 A | 5/1997 | Hay et al. |
| 5,784,148 A | 7/1998 | Heacock |
| 5,790,235 A | 8/1998 | Kirschbaum |
| 5,859,686 A | 1/1999 | Aboutalib et al. |
| 5,989,194 A | 11/1999 | Davenport et al. |
| 6,027,216 A | 2/2000 | Guyton et al. |
| 6,089,715 A | 7/2000 | Hoover et al. |
| 6,095,989 A | 8/2000 | Hay et al. |
| 6,307,526 B1 | 10/2001 | Mann |
| 6,325,765 B1 | 12/2001 | Hay et al. |
| 6,419,638 B1 | 7/2002 | Hay et al. |
| 6,523,954 B1 | 2/2003 | Kennedy et al. |
| 6,595,641 B1 | 7/2003 | Braeuning et al. |
| 6,616,277 B1 | 9/2003 | Davenport |
| 6,663,242 B1 | 12/2003 | Davenport |
| 7,110,582 B1 | 9/2006 | Hay |
| 7,114,808 B2 | 10/2006 | Lai et al. |
| 7,264,355 B2 | 9/2007 | Rathjen |
| 7,284,859 B2 | 10/2007 | Ferguson |
| 7,311,400 B2 | 12/2007 | Wakil et al. |
| 7,374,286 B2 | 5/2008 | Fujeda et al. |
| 7,387,384 B2 | 6/2008 | Heine et al. |
| 7,427,135 B2 | 9/2008 | Chen et al. |
| 7,488,294 B2 | 2/2009 | Torch |
| 7,490,940 B2 | 2/2009 | Lai et al. |
| 7,618,143 B2 | 11/2009 | Clark et al. |
| 7,677,727 B2 | 3/2010 | Shimizu et al. |
| 7,784,940 B2 | 8/2010 | Goldfain et al. |
| 7,798,643 B2 | 9/2010 | Waldorf et al. |
| 7,809,160 B2 | 10/2010 | Vertegaal et al. |
| 7,815,312 B2 | 10/2010 | Matsumura et al. |
| 7,850,307 B2 | 12/2010 | Chen |
| 7,976,162 B2 | 7/2011 | Flitcroft |
| 8,347,106 B2 | 1/2013 | Tsuria et al. |
| 8,534,837 B2 | 9/2013 | Sayeram et al. |
| 8,620,048 B2 | 12/2013 | Nakano et al. |
| 8,950,864 B1 * | 2/2015 | Massengill .......... A61B 5/4064 351/209 |
| 2002/0101568 A1 | 8/2002 | Eberl et al. |
| 2003/0208125 A1 | 11/2003 | Watkins |
| 2005/0043588 A1 | 2/2005 | Tsai |
| 2005/0110949 A1 | 5/2005 | Goldfain et al. |
| 2005/0254008 A1 | 11/2005 | Ferguson et al. |
| 2006/0147095 A1 | 7/2006 | Usher et al. |
| 2007/0174152 A1 | 7/2007 | Bjornberg et al. |
| 2008/0084541 A1 | 4/2008 | Lai et al. |
| 2008/0212027 A1 | 9/2008 | Shimizu |
| 2009/0079937 A1 | 3/2009 | Chen et al. |
| 2009/0115966 A1 | 5/2009 | Waldorf et al. |
| 2009/0316115 A1 | 12/2009 | Itoh et al. |
| 2010/0007850 A1 | 1/2010 | Aggarwala |
| 2010/0149491 A1 | 6/2010 | Chu et al. |
| 2010/0201944 A1 | 8/2010 | Lewis et al. |
| 2010/0245765 A1 | 9/2010 | Dyer et al. |
| 2010/0271595 A1 | 10/2010 | Molebny et al. |
| 2011/0169935 A1 | 7/2011 | Henriksen |
| 2011/0234977 A1 | 9/2011 | Verdooner |
| 2011/0299036 A1 | 12/2011 | Goldenholz |
| 2012/0121158 A1 | 5/2012 | Sekine et al. |
| 2012/0162427 A1 * | 6/2012 | Lynam .................. B60R 1/00 348/148 |
| 2012/0200690 A1 | 8/2012 | Beasley |
| 2012/0212598 A1 * | 8/2012 | Mowrey ................ A61B 3/14 348/78 |
| 2012/0218301 A1 | 8/2012 | Miller |
| 2012/0229617 A1 | 9/2012 | Yates et al. |
| 2012/0249956 A1 | 10/2012 | Narasimha-Iyer et al. |
| 2012/0257163 A1 | 10/2012 | Dyer et al. |
| 2012/0320340 A1 | 12/2012 | Coleman, III |
| 2013/0010260 A1 | 1/2013 | Tumlinson et al. |
| 2013/0016320 A1 | 1/2013 | Naba |
| 2013/0057828 A1 | 3/2013 | de Smet |
| 2013/0169934 A1 | 7/2013 | Verdooner |
| 2013/0176533 A1 | 7/2013 | Raffle et al. |
| 2013/0194548 A1 | 8/2013 | Francis et al. |
| 2013/0208241 A1 | 8/2013 | Lawson et al. |
| 2013/0229622 A1 | 9/2013 | Murase et al. |
| 2013/0234930 A1 | 9/2013 | Palacios Goerger |
| 2014/0022270 A1 | 1/2014 | Rice-Jones et al. |
| 2014/0104573 A1 | 4/2014 | Iwanaga |
| 2015/0223688 A1 | 8/2015 | Wang et al. |
| 2015/0294464 A1 * | 10/2015 | Kim .................. G06K 9/00597 382/117 |
| 2015/0312558 A1 * | 10/2015 | Miller ................ H04N 13/0484 348/54 |
| 2016/0022167 A1 * | 1/2016 | Simon ................ A61B 5/04842 600/301 |
| 2016/0112681 A1 * | 4/2016 | Kaestle .................. A61B 5/11 348/78 |
| 2017/0188823 A1 * | 7/2017 | Ganesan ................ A61B 3/113 |

FOREIGN PATENT DOCUMENTS

| | | |
|---|---|---|
| WO | 2010/080576 A1 | 7/2010 |
| WO | 2012/134272 A1 | 10/2012 |

OTHER PUBLICATIONS

Girdwain, "Goggles Differentiate Between Stroke and Vertigo," Today's Geriatric Medicine, vol. 6 No. 4 p. 8, 2 pages (Oct. 1, 2013).

International Search Report for Application No. PCT/US2012/025665 dated Aug. 31, 2012.

International Search Report and Written Opinion in Application No. PCT/US2015/015124 dated May 15, 2015, 10 pages.

Johns Hopkins Medicine, "Small Johns Hopkins-led study finds portable device diagnoses stroke with 100 percent accuracy," www.hopkinsmedicine.org/se/util/display_mod.cfm?MODULE=/se-server/mod/modules/semod_printpage/mod_default.cfm&PageURL-/news/media/releases/is_i . . . , 2 pages (Mar. 5, 2013).

* cited by examiner

CONCUSSION SCREENING SYSTEM

BACKGROUND

Concussions can be caused by traumatic events like collisions in sports, vehicle accidents, falls, and nearby explosions. As an example, athletes and soldiers engage in activities where concussions can occur with a high probability. Oftentimes, a concussion is ignored or undiagnosed with the consequence that the concussed person does not receive adequate medical treatment. Properly identifying and treating a concussion is important for the long-term health of the person.

SUMMARY

Embodiments of the present disclosure are directed to a concussion screening system. In one aspect, a concussion diagnostic device includes an illumination unit, an image sensor array, a processing unit in communication with the illumination unit and the image sensor array, and a system memory. The system memory includes instructions that, when executed by the processing unit, cause the concussion diagnostic device to: illuminate the illumination unit to display stimuli, receive a plurality of images on the image sensor array, process the plurality of images, and, based on processing the plurality of images, determine whether or not a person is concussed.

In another aspect, a method for determining a concussion status of a person includes displaying stimuli on an illumination unit, where the illumination unit is in communication with a processing unit, receiving a plurality of images on an image sensor array, where the image sensor array is in communication with the processing unit, processing the plurality of images, and, based on the processing of the plurality of images, determining whether or not the person has suffered a concussion.

In yet another aspect, a concussion screening apparatus includes a display, an image sensor array, a processing unit in communication with the display and the image sensor array, and a system memory. The system memory includes instructions that, when executed by the processing unit, cause the concussion screening apparatus to: display stimuli on the display, where the stimuli are associated with a concussion test, receive a plurality of images on the image sensor array, process the plurality of images, based on processing the plurality of images, determine whether a person is concussed, and notify a user of the determination whether or not the person is concussed.

The details of one or more embodiments are set forth in the accompanying drawings and the description below. Other features, objects, and advantages of these embodiments will be apparent from the description, drawings, and claims.

DESCRIPTION OF THE DRAWINGS

The following drawing figures, which form a part of this application, are illustrative of described technology and are not meant to limit the scope of the disclosure as claimed in any manner, which scope shall be based on the claims appended hereto.

DETAILED DESCRIPTION

The present disclosure is directed to systems and methods for performing a determination of whether a person has experienced head trauma, including whether a person is concussed. Generally, eye functioning is impaired in individuals who have suffered a concussion. For example, concussed individuals can experience blurry vision, light sensitivity, eye fatigue, double vision-diplopia, and reading difficulties. Consequently, tests designed to detect whether a person has suffered head trauma ("concussion tests") focus on the eyes' response to stimuli. If a person has suffered a concussion, it can be important that the person receive medical attention. In some instances, it is also important that a concussed person not return immediately to the activity that caused the concussion.

Figure 1:
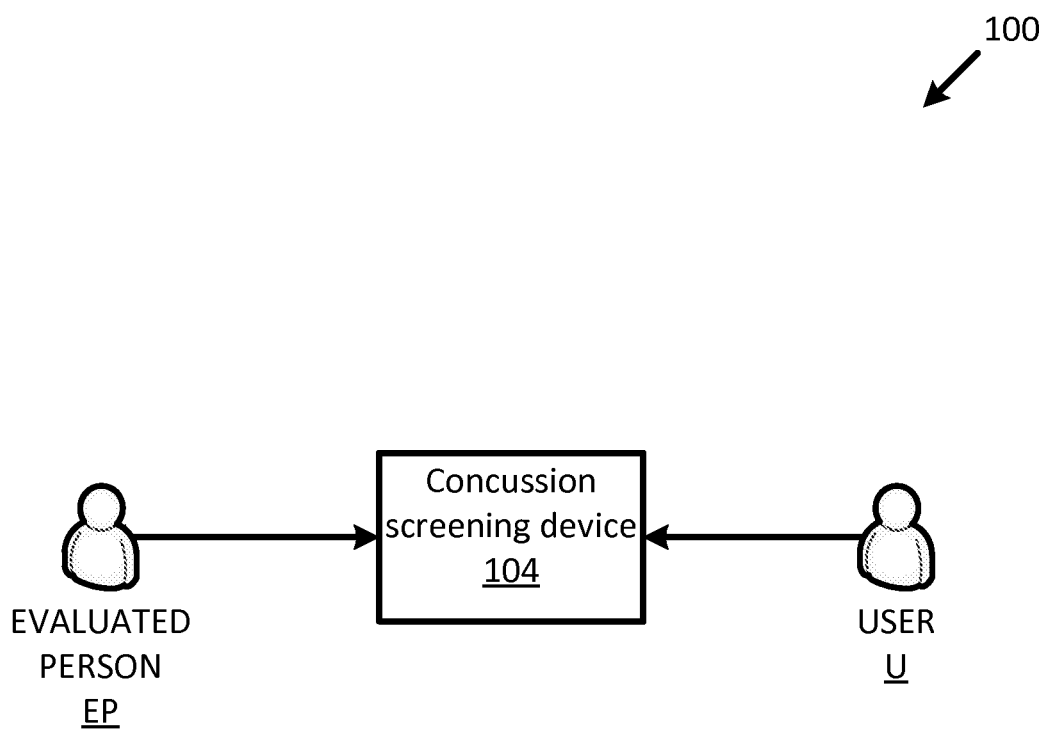
FIG. 1 shows a schematic block diagram of an example concussion determination system.

FIG. 1 illustrates an embodiment of an example concussion determination system 100. The example concussion determination system 100 includes an evaluated person EP, a user U, and a concussion screening device 104. The user U operates the concussion screening device 104 to determine whether the evaluated person EP has suffered a concussion, or to perform a baseline concussion evaluation. Other embodiments can include more or fewer people and components.

An evaluated person EP is a person who may have experienced head trauma. Additionally, an evaluated person EP can be a participant in an activity where head trauma is possible, such as armed services personnel or athletes. In those embodiments, the concussion screening device 104 can be used to create a baseline performance against which the evaluated person's EP performance is later measured. An evaluated person EP can also be someone who has suffered head trauma in a workplace or an automobile accident.

A user U is a person who positions the concussion screening device 104 for an evaluation of the evaluated person EP. In embodiments, the user U is a caregiver that assesses and/or provides medical services, such as an athletic trainer, an armed services medic, an emergency responder, a doctor, a nurse, or a coach. The user U does not necessarily need a medical background in order to operate the concussion screening device 104. In embodiments, the concussion screening device 104 is positioned on a stand or tri-pod and the evaluated person EP initiates the concussion determination on his/her own (i.e., there need not be a user U). Based on the concussion determination, the user U can alert medical personnel or, if the user U has the necessary qualifications, begin treatment him/herself.

In the example concussion determination system 100, the concussion screening device 104 is sized to be a handheld device. As noted above, the concussion screening device 104 can be situated atop a stand or tri-pod. The compact, portable size of the concussion screening device 104 enables its use on-site, such as on an athletic event site (e.g., a football field, a soccer pitch, hockey rink, wrestling arena, etc.), in emergency responders' vehicles, in armed military personnel vehicles, and in clinical/hospital settings. Thus, the portability enables an objective concussion diagnosis shortly after a person suffers head trauma.

The concussion screening device 104 displays one or more concussion tests and detects the evaluated person's EP eye movement. The concussion screening device 104 can be configured to be monocular or binocular. The concussion screening device 104 can be in wireless communication with one or more databases, such as the evaluated person's EP electronic medical record or a table storing the evaluated person's EP baseline test results. U.S. application Ser. No. 13/399,682, filed Feb. 17, 2012, describes systems and methods for photorefraction ocular screening, some of which can be used to implement concussion screening device 104, and that disclosure is hereby incorporated by reference in its entirety. Example configurations of concussion screening device 104, and methods for its use, are shown and described with reference to FIGS. 2-7, below.

Figure 2:
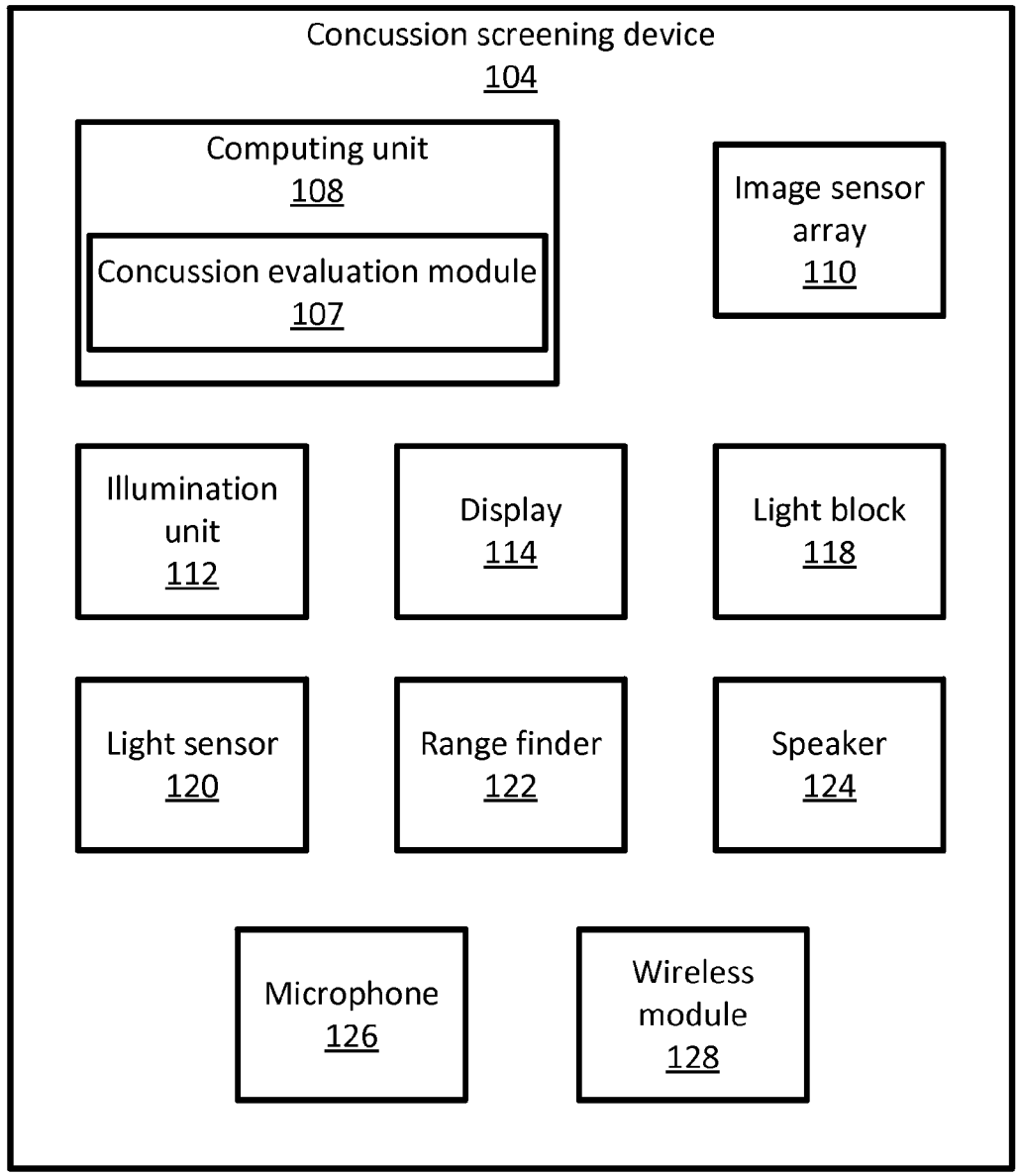
FIG. 2 shows a schematic block diagram illustrating components of example concussion screening device.

FIG. 2 is a schematic block diagram illustrating components of example concussion screening device 104. Example concussion screening device 104 includes a computing unit 108 with a concussion evaluation module 107, an image sensor array 110, an illumination unit 112, a display 114, a light block 118, a light sensor 120, a range finder 122, a speaker 124, a microphone 126, and a wireless module 128. The display 114 is oriented to face the user U and the illumination unit 112 is oriented to face the evaluated person EP. Other embodiments can include more or fewer components.

Figure 7:
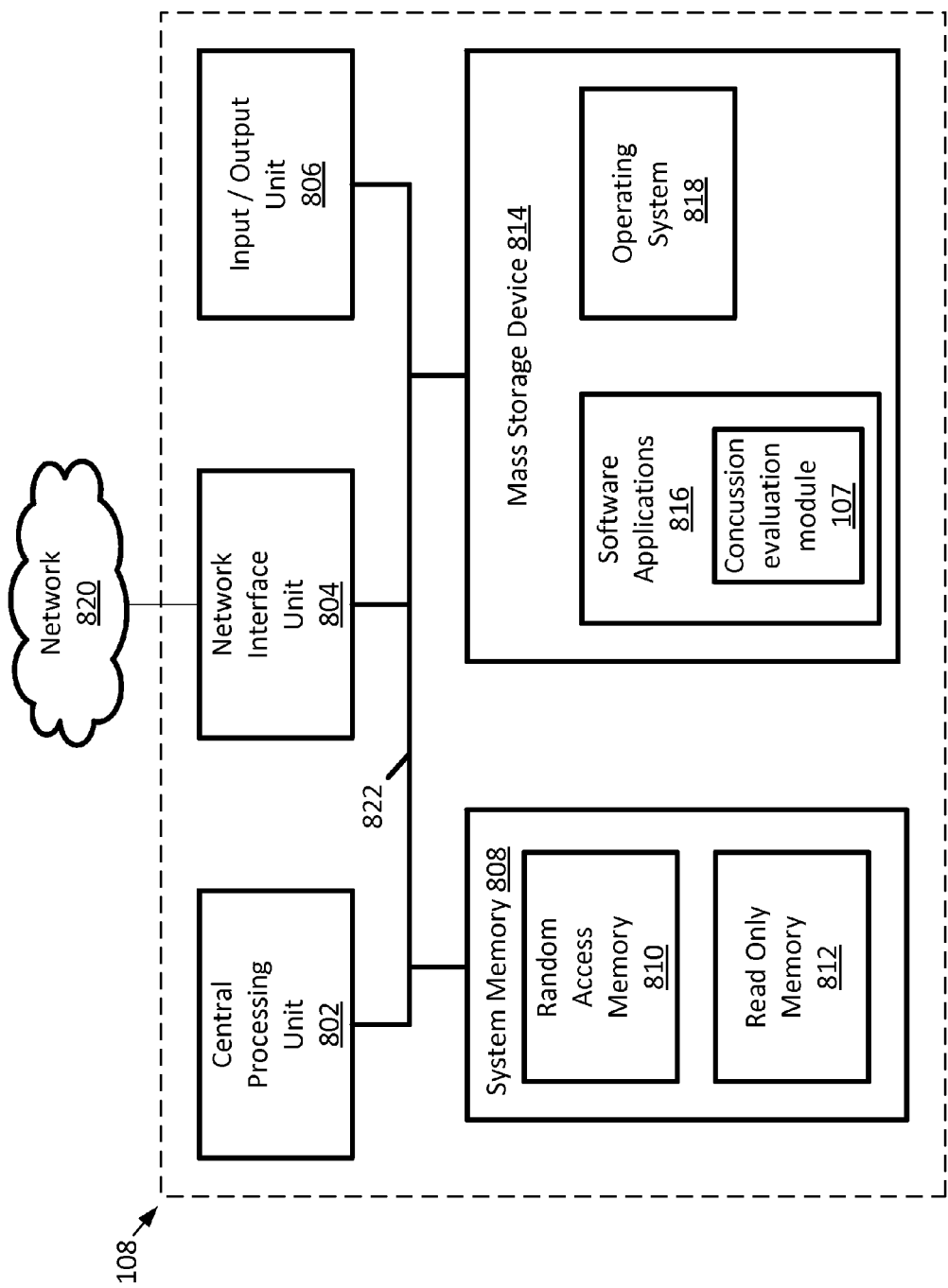
FIG. 7 shows example physical components of a computing device used in the concussion screening device shown in FIG. 2.

Computing unit 108 is in communication with the components of concussion screening device 104, including image sensor array 110, illumination unit 112, display 114, light sensor 120, range finder 122, speaker 124, microphone 126, and wireless module 128. In embodiments where the lens is adjustable, the computing unit 108 is also in communication with a device, such as a mechanical motor, that adjusts the position of the lens. Components of example computing unit 108 are shown in FIG. 7 and described below.

Concussion evaluation module 107 includes, for example, instructions for displaying stimuli on the illumination unit 112, for processing the images received on the image sensor array 110, and for guiding and informing the user U about the concussion status of the evaluated person EP. Stimuli include, for example, a dot, one or more moving dots, designs, colors, changing colors, a video with a focus target, numbers, letters, and information corresponding to a particular type of concussion test.

The combination of displaying stimuli, receiving images, processing the images, and displaying a result is hereinafter referred to as a "concussion test." The concussion evaluation module 107 can be updated with new concussion tests and/or revisions to the concussion tests.

Example concussion tests include pupillometry (which can include varying light levels and determining whether the pupils dilate consistently), eye tracking (which can include determining how the eyes move when shown a moving stimulus and which quadrants might have abnormal movements), reaction time (which can include showing a stimulus and determining a pupil reaction time), recognition of streaming data across the illumination unit (for example, a King-Devick Test), a military acute concussion evaluation (MACE) test, and an audio response quality and time test (which can include an evaluated person speaking in response to displayed stimuli), hippus, double vision, blurred vision, loss of field of view, strabismus, and convergence.

One or more of the tests listed above evaluate, for example, vestibule-ocular reflex (VOR) testing, eye saccades, cortical blind spot mapping, and optokinetic nystagmus (OKN). The results of the test can be compared to, for example, an evaluated person's EP previously-obtained baseline test results, a "normal" result for an average person, or a "gold" standard. Additionally, each pupil's test results can be compared to the other pupil. Normally, in non-concussed persons, both eyes respond to a light stimulus substantially the same.

Another possibility is to present two or more different stimulus conditions at the same time to tax the brain further. For example, during a test an eye stimulus moves laterally while the brightness increases, and pupil constriction is anticipated. Another example of a dual test condition is to apply light stimulus rapidly and determine the ratio of constriction to dilation or vice versa.

Image sensor array 110 receives light and conveys image data to computing unit 108. The image sensor array 110 is, for example, a complementary metal-oxide semiconductor (CMOS) sensor array, also known as an active pixel sensor (APS), or a charge coupled device (CCD) sensor. In embodiments, a lens is supported by the concussion screening device 104 and positioned in front of the image sensor array 110.

Image sensor array 110 has a plurality of rows of pixels and a plurality of columns of pixels. In some embodiments, the image sensor array 110 has about 1280 by 1024 pixels, about 640 by 480 pixels, about 1500 by 1152 pixels, about 2048 by 1536 pixels, or about 2560 by 1920 pixels. The image sensor array 110 is capable of capturing about 25 frames per second (fps); about 30 fps; about 35 fps; about 40 fps; about 50 fps; about 75 fps; about 100 fps; about 150 fps; about 200 fps; about 225 fps; or about 250 fps.

Image sensor array 110 includes photodiodes that have a light-receiving surface and have substantially uniform length and width. During exposure, the photodiodes convert the incident light to a charge. The image sensor array 110 can be operated as a global shutter, that is, substantially all of the photodiodes are exposed simultaneously and for substantially identical lengths of time. Alternatively, the image sensor array 110 is used with a rolling shutter mechanism, in which exposures move as a wave from one side of an image to the other. Other mechanisms are possible to operate the image sensor array 110 in yet other embodiments. Image sensor array 110 is capable of capturing digital images. The digital images can be captured in various formats, such as JPEG, BITMAP, TIFF, etc.

Illumination unit 112 displays one or more concussion tests to the evaluated person EP. Illumination unit 112 includes a light-emitting diode (LED) array having visible LEDs and near-infrared LEDs. The illumination unit 112 is in communication with computing unit 108.

In embodiments, a beam splitter directs the light emitted from the LED array towards the evaluated person. In other embodiments, illumination unit 112 is a display, such as a liquid crystal display (LCD) or active matrix organic light emitting display (AMOLED).

The near-infrared LEDs in the LED array have a wavelength of about 850 nanometers (nm) and are used in capturing pupil images. Generally, the visible LEDs in the LED array have a wavelength of less than about 630 nm. This configuration allows for a visual stimulus to be shown to the evaluated person EP, but not seen in the images captured by the image sensor array 110. In embodiments, the visible LEDs are positioned between, and co-planar with, the near-infrared LEDs in the LED array.

In embodiments, amber LEDs are among the visible LEDs used in illumination unit 112. Amber LEDs have a wavelength of about 608 nm to about 628 nm. The computing unit 108 can regulate the amount of power directed to the LEDs in the LED array. In order to minimize the evaluated person's EP pupil constriction and eye strain, the amber LEDs are illuminated at low to medium power. For example, a 20 mA LED can be run at between about 2 mA to about 10 mA. Alternatively, low brightness amber LEDs can be used, for example, LEDs that run at about 0.5 mA. Additionally, LEDs can be pulse modulated. Visible light LEDs in colors other than amber, when present in the illumination unit 112, can also be operated at low to medium power.

Concussion screening device 104 can record the details of each test environment. For example, concussion screening device 104 records the light intensity of illumination unit 112, contrast levels of illumination unit 112, the quantity of ambient light, time of day, ambient noise level, etc. These data can additionally be used when comparing test results to a baseline test of the evaluated person EP.

Display 114 conveys information to the user U about the positioning of the concussion screening device 104 and of the results of the tests. Display 114 is, for example, a liquid crystal display (LCD) or active matrix organic light emitting display (AMOLED). Display 114 can be touch-sensitive to receive input from the user U.

Information provided to the user U on display 114 includes, for example, the evaluated person's EP distance from the concussion screening device 104, the quality of the focus, the progress of the evaluation, the results of the evaluation, and options for transmitting the results to another database.

Light block 118 is an optional component for limiting the amount of ambient light near the evaluated person's EP eyes. Because the concussion screening device 104 can be used outdoors and in day light, it can be desirable to limit the amount of light near the evaluated person's EP eyes, which causes the pupils to constrict. Additionally, the evaluated person EP may be sensitive to bright light and the dim lighting environment provided by the light block 118 eases some of the evaluated person's EP pain.

Light block 118 can be separate from or integral to the concussion screening device 104. For example, light block 118 is a hood that is placed over the evaluated person's EP head, a booth structure with drapes, or rigid fins with soft material on the exterior that is designed to fit around the evaluated person's EP eyes.

Light sensor 120 detects the ambient light intensity around the concussion screening device 104. Above certain brightness thresholds, the evaluated person's EP pupils constrict to the point where pupil detection is unreliable or impossible. If computing unit 108, in combination with light sensor 120, determines the ambient light is too bright, display 114 communicates to the user U or evaluated person EP to use a light block 118 or move to a lower lighting environment.

Range finder 122, in combination with computing unit 108, determines the distance of the evaluated person EP from the concussion screening device 104. In embodiments, range finder 122 is an infrared transceiver unit, an ultrasonic transceiver unit, or another distance measuring unit known to one of skill in the art. Range finder 122 can be activated by the user U initiating an evaluation.

Generally, the evaluated person EP is positioned about 1 meter (m) from the concussion screening device 104. The concussion screening device 104 provides guidance to the evaluated person EP and/or the user U about how to adjust the relative positioning between the concussion screening device 104 and the evaluated person EP to obtain a focal distance that will yield functional images.

In embodiments where a user U operates the concussion screening device 104, the guidance is displayed on display 114. For example, display 114 can instruct the user U that the evaluated person EP is too close, too far away, or within a proper distance. In embodiments where the concussion screening device 104 is operated as a self-check, the guidance can be communicated to the evaluated person EP using an indicator, such as an LED that is illuminated red until the evaluated person is within a proper focal distance, at which point the LED changes color to green.

In embodiments, the focal length is about, 0.2 m, about 0.3 m, about 0.4 m, 0.5 m, about 0.6 m, about 0.7 m, about 0.75 m, about 0.8 m, about 0.9 m, about 1.0 m.

Speaker 124 communicates to the evaluated person EP and/or user U using speech synthesis. In embodiments, audio is used alone or in combination with illumination unit 112 in the concussion test. Additionally, speaker 124 can be used to guide the evaluated person's EP positioning relative to the concussion screening device 104. In embodiments, the evaluated person EP wears headphones during the concussion test, where audio is communicated to the evaluated person EP through the headphones.

Microphone 126 receives responses spoken by evaluated person EP. In embodiments, the evaluated person EP speaks as part of the concussion test. For example, the evaluated person EP is asked to read a series of numbers or letters shown on the illumination unit 112 and microphone 126 receives the evaluated person's EP responses. Additionally, the evaluated person EP can be asked to state the day, date, month, year, count backwards, state the alphabet backwards, etc. Then computing unit 108, in combination with voice recognition software, decodes the responses and uses the decoded responses in the concussion determination. Data can be evaluated for clarity, order, reverse order, pronunciation, identification, color, or other aspects corresponding to the specific concussion test administered.

Wireless module 128 can connect to external databases to receive and send concussion test data using wireless connections. Wireless connections can include cellular network connections and connections made using protocols such as 802.11a, b, and/or g. In other examples, a wireless connection can be accomplished directly between the concussion screening device 104 and an external display using one or more wired or wireless protocols, such as Bluetooth, Wi-Fi Direct, radio-frequency identification (RFID), or Zigbee. Other configurations are possible.

The communication of data to an external database can enable report printing or further assessment of the evaluated person's test data. For example, data collected and corresponding test results are wirelessly transmitted and stored in a remote database accessible by authorized medical professionals.

Figure 3:
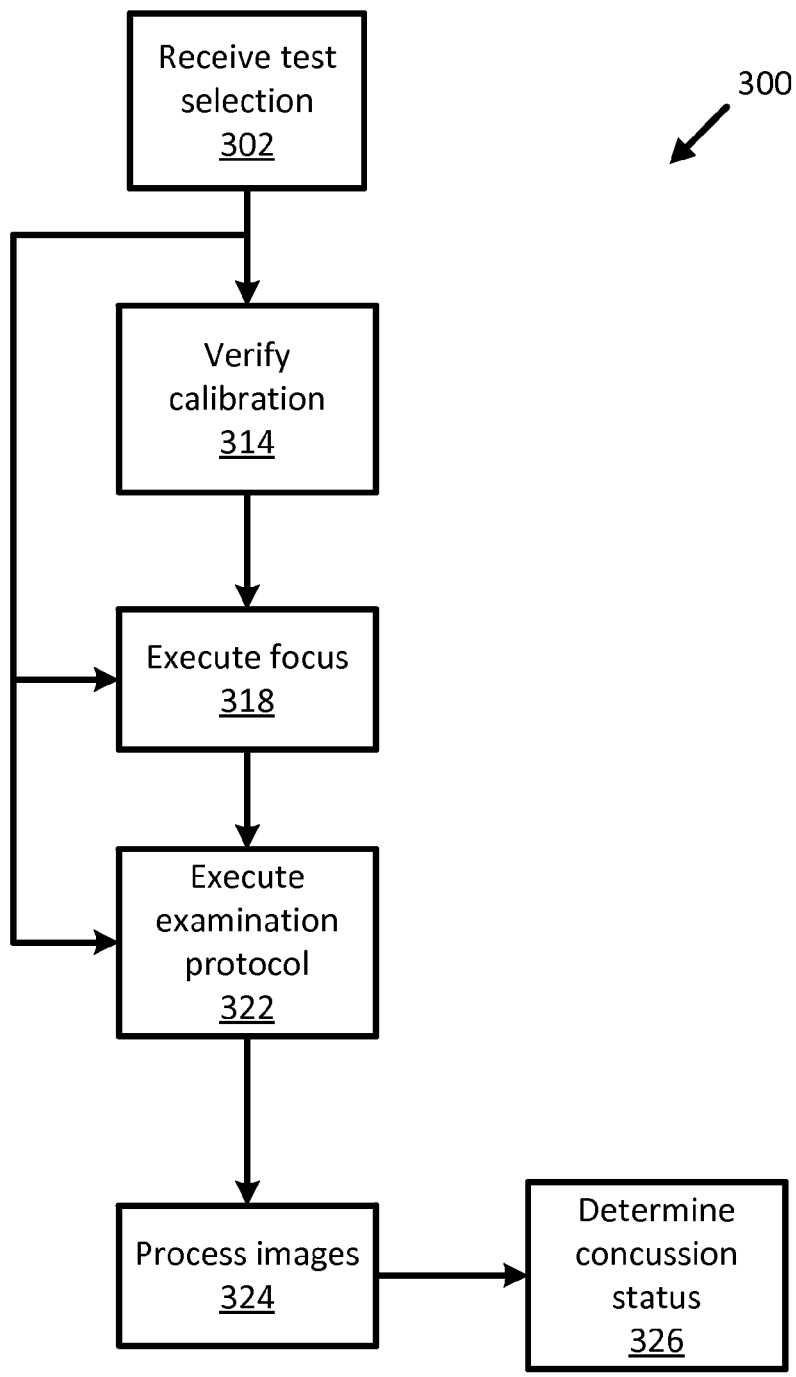
FIG. 3 shows an example method for determining whether an evaluated person has suffered a concussion using the example concussion screening device shown in FIG. 2.

FIG. 3 shows an embodiment of an example method 300 for determining whether an evaluated person has suffered a concussion using the example concussion screening device 104. The example method 300 includes receiving a test selection (operation 302), executing calibration (operation 314), executing focus (operation 318), executing examination protocol (operation 322), processing images (operation 324), and determining concussion status (operation 326). In embodiments, the example method 300 is used to create baseline test results for an evaluated person that has not recently suffered a concussion. Other embodiments can include more or fewer operations.

The example method 300 begins when the concussion screening device 104 receives a request for a test (operation 302). As mentioned above, the concussion screening device 104 can be used to perform a baseline test or a concussion test. A user U or an evaluated person EP initiates the test using a display 114 on the concussion screening device 104.

In embodiments, the concussion screening device 104 prompts the user U or evaluated person EP to enter information about the evaluated person EP, such as name, identification number, age, gender, activity, height, and weight, to name a few examples. This information can be entered using a display 114 that is touch-sensitive.

In embodiments, the concussion screening device 104 prompts the user U or evaluated person EP to select a concussion test type. Example concussion tests are listed and described above with reference to FIG. 2.

After receiving the request for a test (operation 302), the concussion screening device 104 either verifies a calibration (operation 314), executes focus (operation 318), or executes the examination protocol (operation 322). In embodiments, the concussion screening device 104 is not calibrated, thus the next operation after operation 302 is to verify a calibration (operation 314). In embodiments, the concussion screening device 104 is calibrated but not focused, thus the next operation after operation 302 is to execute focus (operation 318). In embodiments, the concussion screening device 104 is calibrated and focused and the next operation after operation 302 is to execute examination protocol (operation 322).

Verify calibration (operation 314), execute focus (operation 318), execute examination protocol (operation 322), and process images (operation 324) are shown and described in more detail below with reference to FIGS. 4, 5, 6, and 7, respectively.

After processing images (operation 324), the concussion screening device 104 determines a concussion status (operation 326). During operation 326, the pupil movement identified in operation 324 is compared and scored against the relevant test criteria. For example, in an embodiment where the test includes a moving stimulus, the position of the pupils can be correlated to the known position of the stimulus across the plurality of images captured during the test. Additionally, or alternatively, the position of the pupils during the test can be mapped and the overall movement of the eyes, irrespective of the moving stimulus position, can be evaluated against the test criteria.

Some tests rely upon baseline test results for a concussion determination (operation 326). That is, when an evaluated person's EP test results vary widely enough from their non-concussed test result, the likely result in operation 326 is that the person has suffered a concussion. Additionally or alternatively, concussion determination (operation 326) includes a clinician evaluating the test results and making their own determination regarding the evaluated person's EP concussion status.

Figure 4:
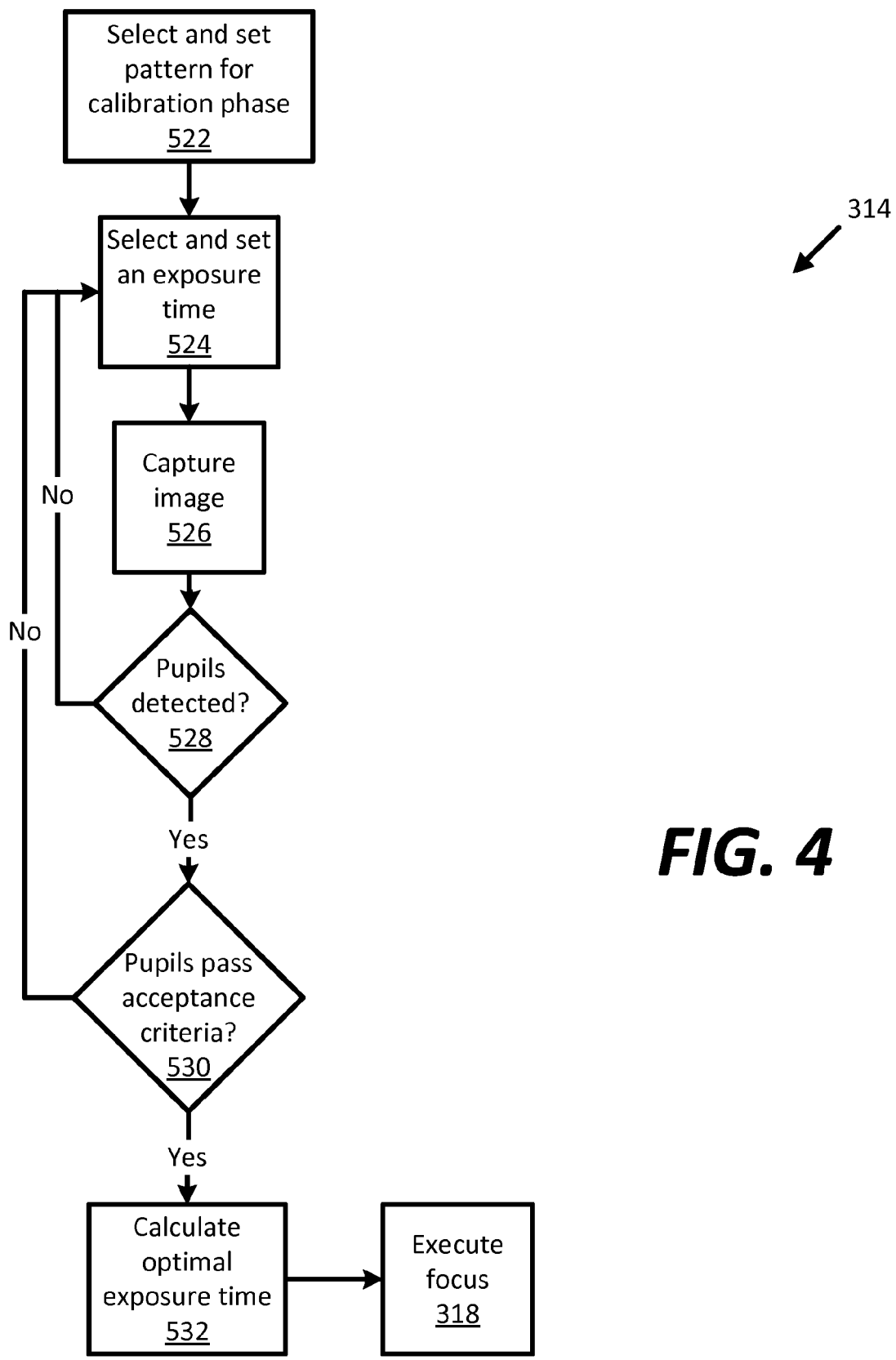
FIG. 4 shows an example method for executing calibration during the method shown in FIG. 3.

FIG. 4 illustrates an embodiment of calibrating the concussion screening device 104 (operation 314). Verifying the calibration protocol (operation 314) includes selecting and setting a pattern for the calibration phase (operation 522), selecting and setting an exposure time (operation 524), capturing image (operation 526), determining whether pupils were detected (decision 528), determining whether the pupils pass acceptance criteria (decision 530), calculating optimal exposure time (operation 532), and proceeding to execute focus (operation 318). Other embodiments can include more or fewer operations.

Verifying calibration (operation 314) begins by selecting and setting a pattern suited for the calibration phase. Calibration (operation 314) can include ensuring that the image sensor array's 110 focus can adjust to the proper focal distance to the pupil throughout the complete capable rang, that the light intensity is controlled properly, and that the ambient light measurement sensor 120 is operative.

After the pattern is set (operation 522), an exposure time is selected and set for testing (operation 524). Using the selected exposure time, the concussion screening device 104 captures an image (operation 526) and a determination is made whether pupils are detected in the captured image (decision 528). If pupils are not detected in the captured image, then operation 314 can return to selecting and setting a different exposure time (operation 524). Using a newly selected exposure time, the concussion screening device 104 again captures an image and a determination is made whether the pupils are detected in the captured image (decision 528).

If pupils are detected, the viability of the selected exposure time is further tested by undergoing a second determination whether the pupils pass predetermined acceptance criteria (decision 530). Acceptance criteria in decision 530 include, for example, a suitable presence of pupils necessary to perform calibration, an acceptable pupil size having a measurable diameter ranging between 1.5 to 10 mm, an acceptable inter-pupil distance between pupil centers, an acceptable examinee distance from concussion screening device 104, an acceptable pupil saturation level or combinations thereof.

If the pupils fail to satisfy one or more predefined acceptance criteria (decision 530), then operation 314 again returns to select and set another exposure time (operation 524). The process repeats to determine which exposure time provides images where pupils are detected without saturation. Generally, saturation is defined as greater than 10% of the pixels in the pupil have an intensity value greater than 98% of the maximum value associated with the image sensor array 110.

When the pupil image passes decision 530, next the optimal exposure time is calculated (operation 532). The optimum exposure time can be set to 75% of the full sensor range. Once the pupils are detected and located, a central pixel strip, for example, a 25×11 pixel strip, is measured for brightness. The brightness measure is the mean pupil intensity in the strip. Given the mean pupil intensity value, the optimum exposure time is calculated as follows:

$$time_{optimum\ exposure} = \frac{767.25(time_{current\ exposure})}{MeanPupilIntensity}$$

When both pupils are included in an evaluation, the pupil with the brightest mean intensity value can be used in the calculation.

Figure 5:
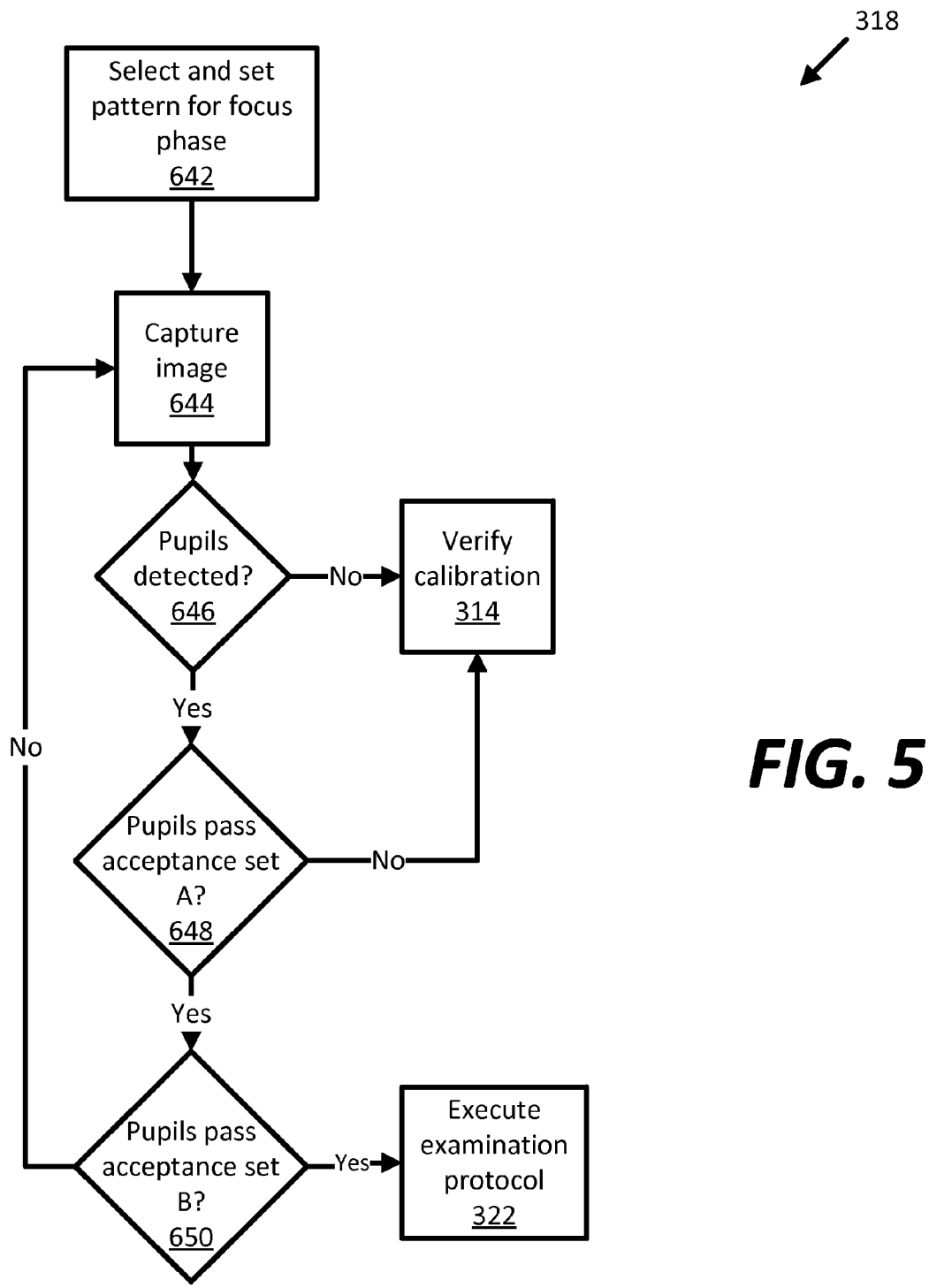
FIG. 5 shows an example method for executing focus during the method shown in FIG. 3.

After calculating an optimal exposure time (operation 532), a focus process is executed (operation 318). FIG. 5 illustrates an embodiment of a focus process (operation 318). Obtaining an acceptable focus enables an accurate determination of the pupil positions.

Focus determination (operation 318) begins by selecting and setting a pattern suited for the focus phase (operation 642). After the pattern is set (operation 642), the concussion screening device 104 captures an image (operation 644) and determines whether pupils are detected in the captured image (decision 646). If pupils are not detected, focus determination (operation 318) can return to verify calibration (operation 314). If pupils are detected, the concussion screening device 104 assesses whether the captured images pass a first set (decision 648) and a second set (decision 650) of acceptance criteria.

The first set of acceptance criteria used in decision 648 can be similar to the acceptance criteria used in calibration (operation 314). That is, whether there is a suitable presence of pupils, an acceptable pupil size and acceptable inter-pupil distance. If the detected pupils fail to satisfy the first set of acceptance criteria, then focusing (operation 318) can again revert to the calibration (operation 314) to reinitiate the calibration phase. If the detected pupils satisfy the first set of acceptance criteria, then the detected pupils are tested against the second set of acceptance criteria (decision 650).

The second set of acceptance criteria includes determining whether the pupil images include a glint or an acceptable gaze direction (decision 650). If the pupils do not pass the second set of acceptance criteria, then concussion screening device 104 can capture a new image (operation 644). If the pupils pass the second set of acceptance criteria, the calibration (operation 314) and focus (operation 318) phases are complete and method 300 proceeds with executing an examination protocol (operation 322).

Figure 6:
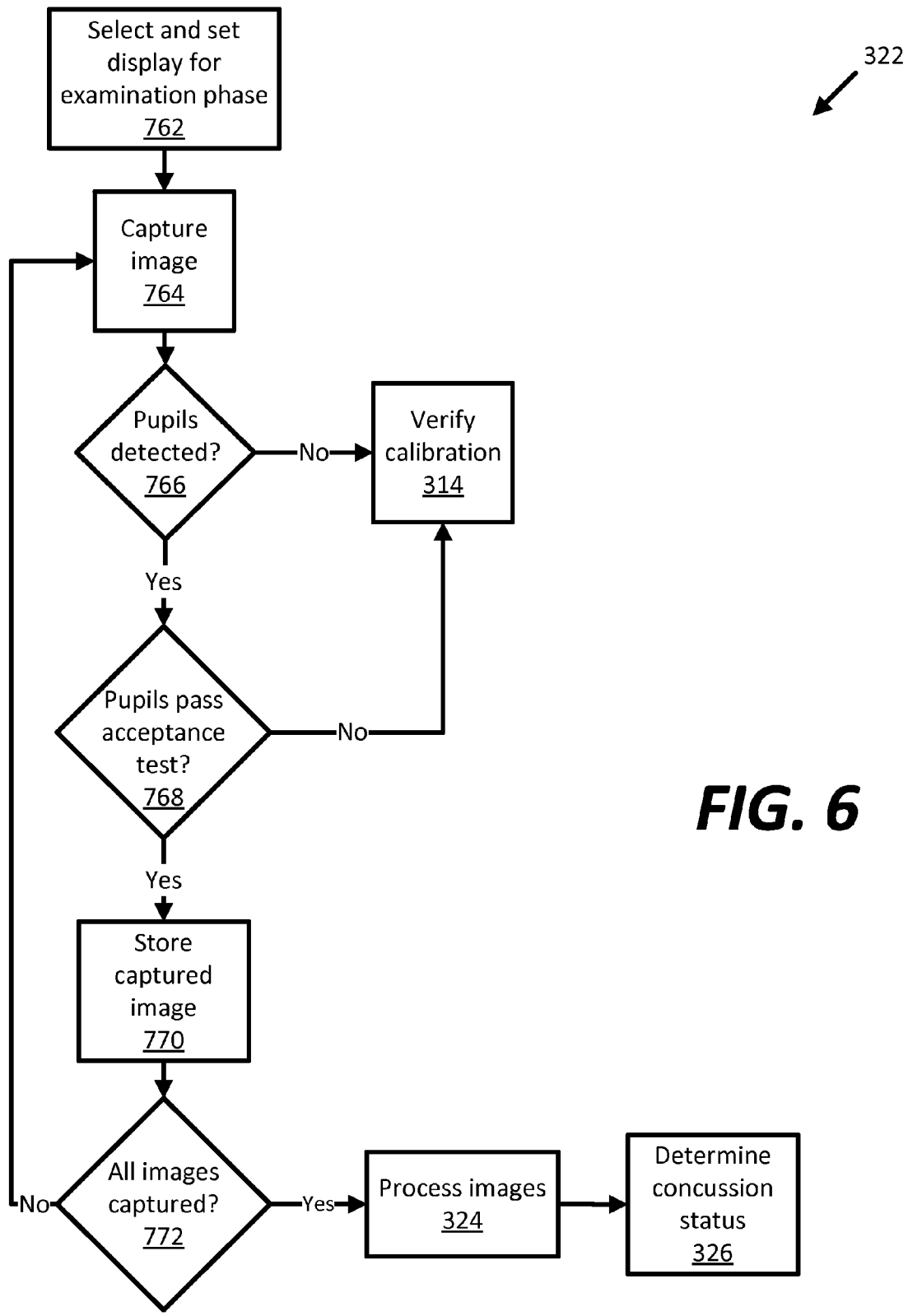
FIG. 6 shows an example method for executing calibration during the method shown in FIG. 3.

FIG. 6 illustrates an embodiment of an examination protocol (operation 322). The criteria for determining image suitability are stricter than in the calibration (operation 314) and focus (operation 318) phases. In addition to standard image measures, changes in some images measures may be performed to reduce the possibility of blur in the images. Changes in image measures are preferably performed between a current image and a reference image, which is typically the image preceding the current image.

Examination protocol (operation 322) begins by selecting and setting a display (operation 762). The display is based on and includes the relevant components of the concussion test selected by the user, which was received by concussion screening device 104 in operation 302. During display (operation 762), concussion screening device 104 captures an image (operation 764). If concussion screening device 104 detects pupils in the image (decision 766), then the image is evaluated against an acceptance test (decision 768). If the pupils are not detected, the examination protocol (operation 322) can return to the calibration (operation 314) phase.

The acceptance test (decision 768) can be the same test as described above in the focus phase (operation 318). If the pupils do not satisfy one or more of the acceptance criteria, examination protocol (operation 322) can return to the calibration (operation 314) phase or the focus phase (operation 318), depending upon the criteria failed.

Criteria failures resulting in a return to the calibration (operation 314) phase may include, but are not limited to, absence of pupils in the current image, unacceptable pupil size(s) in either the current or reference images, unacceptable change in pupil size between current and reference images, unacceptable inter-pupil distance in the current image, unacceptable change in the inter-pupil distance between current and reference images, or unacceptable gaze direction in either the current and reference images. Criteria failures resulting in a return only to the focus (operation 318) process may include, but are not limited to, absence of pupils in the reference image, unacceptable change in pupil position between current and reference images, unacceptable inter-pupil distance in the reference image, unacceptable glint position(s) in either the current and reference images, unacceptable change in glint position(s) between current and reference images, or unacceptable change in gaze direction between current and reference images.

If the image passes the acceptance criteria, the concussion screening device 104 stores the captured image (operation 770) for use in the concussion determination analysis. After storing the captured image (operation 770), the concussion screening device 104 determines whether additional images need to be captured (operation 772). Examination protocol (operation 322) repeats until all images are captured.

Next, the concussion screening device 104 processes the images (operation 324) and determines the concussion status of the evaluated person (operation 326). Image processing protocol (operation 324) identifies the pupils in each captured image using, for example, the process described in U.S. patent application Ser. No. 13/399,682, noted above as incorporated by reference in its entirety.

After pupils are identified, the evaluated person's EP gaze direction is also determined. The gaze direction is mapped over the duration of the concussion test and can be compared to the expected values. As discussed above, the movement of the pupils during the concussion test identified in operation 324 is used in concussion status determination (operation 326).

FIG. 7 shows an example computing unit 108 hosting the concussion evaluation module 107. As illustrated, the example computing unit 108 includes at least one central processing unit ("CPU") 802, a system memory 808, and a system bus 822 that couples the system memory 808 to the CPU 802. The system memory 808 includes a random access memory ("RAM") 810 and a read-only memory ("ROM") 812. A basic input/output system that contains the basic routines that help to transfer information between elements within the example computing unit 108, such as during startup, is stored in the ROM 812. The example computing unit 108 further includes a mass storage device 814. The mass storage device 814 is able to store software instructions and data.

The mass storage device 814 is connected to the CPU 802 through a mass storage controller (not shown) connected to the system bus 822. The mass storage device 814 and its associated computer-readable data storage media provide non-volatile, non-transitory storage for the example computing unit 108. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing unit 108.

According to various embodiments of the inventions, the example computing unit 108 may operate in a networked environment using logical connections to remote network devices through the network 820, such as a wireless network, the Internet, or another type of network. The example computing unit 108 may connect to the network 820 through a network interface unit 804 connected to the system bus 822. It should be appreciated that the network interface unit 804 may also be utilized to connect to other types of networks and remote computing systems. The example computing unit 108 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, the mass storage device 814 and the RAM 810 of the example computing unit 108 can store software instructions and data. The software instructions include an operating system 818 suitable for controlling the operation of the example computing unit 108. The mass storage device 814 and/or the RAM 810 also store software instructions, that when executed by the CPU 802, cause the example computing unit 108 to provide the functionality of the example computing unit 108 discussed in this document. For example, the mass storage device 814 and/or the RAM 810 can store software instructions that, when executed by the CPU 802, cause the example computing unit 108 to display received data on the display screen of the example computing unit 108.

The description and illustration of one or more embodiments provided in this application are not intended to limit or restrict the scope of the inventions as claimed in any way. The embodiments, examples, and details provided in this application are considered sufficient to convey possession and enable others to make and use the best mode of claimed inventions. The claimed inventions should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed inventions and the general inventive concept embodied in this application that do not depart from the broader scope.

The invention claimed is:

1. A concussion diagnostic device, comprising:
   an illumination unit including a first display;
   a rear display;
   an image sensor array;
   a light sensor;
   a range finder;
   a central processing unit in communication with the illumination unit, the light sensor, the range finder, and the image sensor array; and
   system memory, the system memory including instructions that, when executed by the processing unit, cause the concussion diagnostic device to:
      when the concussion diagnostic device is not calibrated, execute a calibration sequence, the calibration sequence including to:
         determine whether or not pupils are detected in a calibration image; and
         determine whether or not the pupils pass acceptance criteria;
      on the rear display:
         provide guidance to a user in positioning the concussion diagnostic device relative to a person to obtain a focal distance, the positioning based on a distance determined by the range finder; and
         provide guidance to move to a lower lighting environment when the light sensor detects an ambient light intensity above a brightness threshold;
      illuminate the illumination unit to display stimuli on the first display;
      on the image sensor array, receive a plurality of images;
      process the plurality of images;
      based on processing the plurality of images, determine whether or not the person is concussed; and
      on the rear display, display the determination whether the person is concussed.

2. The concussion diagnostic device of claim 1, wherein the illumination unit includes a plurality of light-emitting diodes (LEDs).

3. The concussion diagnostic device of claim 2, wherein the plurality of LEDs include amber LEDs; and
   wherein the illumination unit is configured to operate the amber LEDs at low to medium power.

4. The concussion diagnostic device of claim 2, wherein processing the plurality of images includes detecting a state of a pupil of the person.

5. The concussion diagnostic device of claim 4, further comprising a light block.

6. The concussion diagnostic device of claim 1, wherein the system memory further includes instructions that, when executed by the processing unit, cause the illumination unit to display a concussion test.

7. The concussion diagnostic device of claim 6, wherein the image sensor array is capable of capturing at least 20 frames per second.

8. The concussion diagnostic device according to claim 1, wherein the system memory further includes instructions that, when executed by the processing unit, cause the concussion diagnostic device to:
   determine calibration phase stimuli;
   display the calibration phase stimuli; and
   determine an optimal exposure time.

9. A method for determining a concussion status of a person with a concussion diagnostic device, the method comprising:
   when the concussion diagnostic device is not calibrated, executing a calibration sequence, the calibration sequence including:
      determining whether or not pupils are detected in a calibration image; and
      determining whether or not pupils pass acceptance criteria;
   on a rear display:
      providing guidance to a user in positioning the concussion diagnostic device relative to the person to obtain a focal distance, the positioning based on a distance determined by a range finder; and
      providing guidance to move to a lower lighting environment when a light sensor detects an ambient light intensity above a brightness threshold;
   displaying stimuli on an illumination unit, wherein the illumination unit is in communication with a processing unit;

receiving a plurality of images on an image sensor array, wherein the image sensor array is in communication with the processing unit;
processing the plurality of images;
based on processing the plurality of images, determining whether or not the person has suffered a concussion;
on the rear display, displaying a determination whether the person has suffered the concussion.

10. The method of claim 9, wherein the processing of the plurality of images includes detecting a state of a pupil of the person.

11. The method of claim 10, wherein the processing of the plurality of images further includes determining a motion of the pupil across the plurality of images.

12. The method of claim 11, wherein the processing of the plurality of images further includes comparing the motion of the pupil to a criteria; and
wherein the determining whether the person has suffered the concussion is based on comparison of the motion of the pupil to the criteria.

13. The method of claim 9, wherein displaying stimuli includes illuminating a plurality of amber light-emitting diodes; and
further comprising notifying the user of the determination whether the person has suffered the concussion.

14. The method according to claim 9, further comprising:
determining calibration phase stimuli;
displaying the calibration phase stimuli; and
determining an optimal exposure time.

15. A concussion screening apparatus, comprising:
a first display, wherein the first display includes a plurality of light-emitting diodes (LEDs) including near-infrared LEDs;
an image sensor array;
a light sensor;
a range finder;
a processing unit in communication with the first display, the light sensor, the range finder, and the image sensor array;
a rear display in communication with the processing unit; and
system memory, the system memory including instructions that, when executed by the processing unit, cause the concussion screening apparatus to:
when the concussion diagnostic device is not calibrated, execute a calibration sequence, the calibration sequence including to:
determine whether or not pupils are detected in a calibration image; and
determine whether or not pupils pass acceptance criteria;
on the rear display:
provide guidance to the user in positioning the concussion screening apparatus relative to a person to obtain a focal distance, the positioning based on a distance determined by the range finder; and
provide guidance to move to a lower lighting environment when the light sensor detects an ambient light intensity above a brightness threshold;
communicate the guidance to the evaluated person using an indicator that illuminates until the person is within the focal distance;
display stimuli on the first display, wherein the stimuli are associated with a concussion test;
receive a plurality of images on the image sensor array;
process the plurality of images;
based on processing the plurality of images, determine whether a person is concussed; and
on the rear display, notify a user of the determination whether or not the person is concussed.

16. The concussion screening apparatus of claim 15, further comprising a light-blocking element; and
wherein the image sensor array is capable of capturing at least 20 frames per second.

17. The concussion screening apparatus of claim 15, wherein the first display further includes a plurality of amber LEDs; and
wherein the first display is configured to operate the plurality of amber LEDs at low to medium power.

18. The concussion screening apparatus of claim 17, further comprising:
a microphone in communication with the processing unit, wherein the system memory further includes instructions that, when executed by the processing unit, cause the concussion screening apparatus to:
process spoken words received by the microphone.

19. The concussion screening apparatus of claim 18, wherein processing the plurality of images includes detecting a pupil of the person.

20. The concussion screening apparatus of claim 19, wherein the processing of the plurality of images further includes:
determining a motion of the pupil across the plurality of images;
comparing the motion of the pupil to a criteria; and
wherein the determining whether the person is concussed is based on comparison of the motion of the pupil to the criteria.

* * * * *